(12) United States Patent
Zhao

(10) Patent No.: US 11,992,186 B2
(45) Date of Patent: May 28, 2024

(54) ENDOSCOPE WITH OPTICAL FILTER ARRANGEMENT AND USE

(71) Applicant: OLYMPUS WINTER & IBE GMBH, Hamburg (DE)

(72) Inventor: Jianxin Zhao, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 241 days.

(21) Appl. No.: 17/002,921

(22) Filed: Aug. 26, 2020

(65) Prior Publication Data

US 2021/0059509 A1  Mar. 4, 2021

(30) Foreign Application Priority Data

Aug. 28, 2019 (DE) .......................... 102019123053.5

(51) Int. Cl.
*A61B 1/00* (2006.01)
*A61B 1/05* (2006.01)

(52) U.S. Cl.
CPC ...... *A61B 1/00186* (2013.01); *A61B 1/00193* (2013.01); *A61B 1/00195* (2013.01); *A61B 1/05* (2013.01)

(58) Field of Classification Search
CPC ............ A61B 1/00186; A61B 1/00193; A61B 1/00195; A61B 1/05; G02B 5/208; G02B 23/2415; G02B 23/243; G02B 23/2407; G02B 26/007
See application file for complete search history.

(56) References Cited

U.S. PATENT DOCUMENTS 3,804,081 A * 4/1974 Kinoshita .......... A61B 1/00165
385/119
4,878,113 A 10/1989 Nakamura
5,067,805 A * 11/1991 Corle ................. G02B 21/0044
359/638

(Continued)

FOREIGN PATENT DOCUMENTS

CN 102469918 A 5/2012
CN 102469932 A 5/2012

(Continued)

OTHER PUBLICATIONS

Japanese Office Action dated Jun. 10, 2022 received in 2020-142775.

*Primary Examiner* — Anh Tuan T Nguyen
*Assistant Examiner* — Shankar Raj Ghimire
(74) *Attorney, Agent, or Firm* — Scully, Scott, Murphy & Presser, P.C.

(57) ABSTRACT

An endoscope including: an optical filter arrangement having: a holder; and an optical filter having one of different filter properties in different directions or multiple optical filters with different filter properties, the optical filter being arranged in the holder to rotate about an axis of rotation in at least one beam path of the endoscope in a direction of light incidence in or behind an objective of the endoscope and in front of an image capturing unit or an eyepiece; wherein the optical filter arrangement is configured to change from a first filter property to a second filter property when the optical filter is rotated by 90° about the axis of rotation from a first target rotational position to a second target rotational position.

12 Claims, 3 Drawing Sheets

(56) References Cited

U.S. PATENT DOCUMENTS

| | | | |
|---|---|---|---|
| 6,700,690 B1* | 3/2004 | Buchsbaum | G02B 5/20 |
| | | | 359/578 |
| 6,821,245 B2* | 11/2004 | Cline | A61B 1/06 |
| | | | 600/181 |
| 8,675,285 B2* | 3/2014 | Obrebski | G02B 26/007 |
| | | | 359/672 |
| 11,160,444 B1* | 11/2021 | D'Aquanni | A61B 1/317 |
| 2002/0049366 A1 | 4/2002 | Kehr | |
| 2005/0168751 A1* | 8/2005 | Horii | G01N 21/4795 |
| | | | 356/479 |
| 2005/0286024 A1* | 12/2005 | Gupta | G03B 21/208 |
| | | | 348/E5.139 |
| 2006/0206003 A1* | 9/2006 | Hoeg | G02B 27/642 |
| | | | 600/117 |
| 2006/0206006 A1* | 9/2006 | Schara | A61B 1/042 |
| | | | 600/173 |
| 2006/0291061 A1 | 12/2006 | Iyama et al. | |
| 2010/0030031 A1* | 2/2010 | Goldfarb | A61B 1/00183 |
| | | | 600/173 |
| 2011/0267678 A1* | 11/2011 | Erdogan | G02B 26/007 |
| | | | 359/290 |
| 2011/0299174 A1 | 12/2011 | Obrebski | |
| 2012/0035422 A1* | 2/2012 | Lei | A61B 1/00163 |
| | | | 600/173 |
| 2012/0257030 A1 | 10/2012 | Lim et al. | |
| 2013/0162775 A1* | 6/2013 | Baumann | A61B 5/065 |
| | | | 348/45 |
| 2013/0231606 A1* | 9/2013 | Stearns | A61M 13/003 |
| | | | 604/26 |
| 2013/0321921 A1* | 12/2013 | Belgum | G02B 7/005 |
| | | | 359/578 |
| 2014/0066781 A1* | 3/2014 | Park | A61B 1/00186 |
| | | | 600/475 |
| 2014/0254006 A1* | 9/2014 | Weiger | G02B 23/243 |
| | | | 359/434 |
| 2014/0275785 A1* | 9/2014 | Kesten | A61B 1/00183 |
| | | | 600/117 |
| 2014/0307311 A1* | 10/2014 | Serrels | G02B 21/002 |
| | | | 359/387 |
| 2016/0178886 A1* | 6/2016 | Shechterman | A61B 1/00096 |
| | | | 348/45 |
| 2017/0167980 A1* | 6/2017 | Dimitriadis | A61B 3/14 |
| 2017/0280980 A1* | 10/2017 | Yasunaga | A61B 1/00183 |
| 2018/0067389 A1* | 3/2018 | Kikuma | F21V 7/0066 |
| 2019/0054217 A1* | 2/2019 | Axon | A61B 10/0283 |
| 2019/0059706 A1* | 2/2019 | Lin | A61B 1/00096 |
| 2019/0113456 A1* | 4/2019 | Yamada | G02B 21/16 |
| 2019/0208997 A1* | 7/2019 | Rout | A61B 1/0646 |
| 2020/0147601 A1* | 5/2020 | Briggs | B01L 3/02 |
| 2021/0059509 A1* | 3/2021 | Zhao | G02B 23/243 |

FOREIGN PATENT DOCUMENTS

| | | | |
|---|---|---|---|
| CN | 104080389 A | | 10/2014 |
| DE | 19713276 A1 | | 10/1998 |
| DE | 102009011681 A1 | | 8/2010 |
| DE | 102015003681 A1 | | 9/2016 |
| JP | H02-32313 A | | 2/1990 |
| JP | H08-106059 A | | 4/1996 |
| JP | 2002-330320 A | | 11/2002 |
| JP | 2005-070366 A | | 3/2005 |
| JP | 2008-259591 A | | 10/2008 |
| JP | 2010-128459 A | | 6/2010 |
| JP | 2010128459 A | * | 6/2010 |
| JP | 2017-094124 A | | 6/2017 |

* cited by examiner

ENDOSCOPE WITH OPTICAL FILTER ARRANGEMENT AND USE

CROSS-REFERENCE TO RELATED APPLICATION

The present application is based upon and claims the benefit to DE 10 2019 123 053.5 filed on Aug. 28, 2019, the entire contents of which are incorporated herein by reference.

BACKGROUND

Field

The present disclosure relates to an endoscope with an optical filter arrangement and to a use of an optical filter arrangement in an endoscope.

Prior Art

Endoscopes are used for optical examination, in the medical field among others, wherein in many cases optical filters are used to realize special examination modalities. Optical filters include color filters as well as band-pass or edge filters, polarization filters, and UV and infrared filters (IR filters). The latter make it possible to take advantage of the fact is that endoscopes can also be used in the infrared range, for example for the use of fluorescence angiography by means of indocyanine green, the fluorescence spectrum of which lies in the near-infrared range. In the applicant's IR laparoscopes, an IR filter is positioned between the field of view and the eyepiece.

For various uses, doctors therefore have to have two different laparoscopes for normal laparoscopy with visible light and for infrared laparoscopy and change between them. It would therefore be desirable to be able to carry out both uses with one endoscope.

An endoscope device is known from US 2012/0257030 in which light from a light source is alternately conducted through different color filters arranged in a filter wheel so that the illumination light already has the corresponding color characteristic. Since the filter wheel is larger than the white light source, this device is fairly large. An endoscope device is known from U.S. Pat. No. 4,878,113 A which also has a filter wheel at the light source with different colored filters in the visible spectrum.

A device for capturing an image of an object field on a human or animal body is known from DE 10 2015 003 681 A1, which device has a pivotable filter that can be pivoted into and out of the beam path by pivoting about a pivoting axis which is oriented perpendicular to the longitudinal axis of the beam path of the device. In this way, filtering occurs in one pivot state and no filter occurs in the other pivot state.

FIG. 1 schematically shows a cross-section of a part of an endoscope 10 which is known from the prior art. This is an IR laparoscope with an endoscope shaft (not shown) with an objective 13 or possibly a series of lens reversal systems that are arranged along an optical axis 22 or central axis of the optical system of the endoscope 10. The part shown is located in the handle of the endoscope 10, on the housing 14 of which an illumination unit 18 is also present which generates light that is introduced into optical fibers guided distally (without reference sign). The light that is propagated from the left through the endoscope 10 through the partially shown shaft 12 reaches an optical filter 20 configured as an IR filter through which only the spectral portions of the light in the IR range that were not filtered out are let through and enter the lens group of the eyepiece 16. The optical filter 20 remains in the beam path so that the filter properties in this endoscope 10 are established.

FIG. 6 shows a beam path of a sideways-facing stereo endoscope according to the state of the art. This has an input lens system 202 with a curved input window and an in-put lens, as well as a deflection prism unit 204 to which a further lens as well as two parallel lens systems 206 of a first beam path 220 and of a second beam path 222 attach. One optical filter 210, 212, which can be configured, for example, as an infrared filter, is arranged in each case between the lens arranged directly behind the deflection prisms 204 and the parallel lens systems 206. FIG. 7a shows the filter arrangement from the optical system 200 in FIG. 6 in a front view.

SUMMARY

An object is, in contrast to the prior art, to realize different filter properties in a single endoscope without needing to increase the size of the endoscope.

Such object can be solved by an endoscope with an optical filter arrangement which comprises in a holder an optical filter which has different filter properties in different directions or multiple optical filters with different filter properties, and is arranged rotatably about an axis of rotation in at least one beam path of the endoscope in the direction of light incidence in or behind an objective of the endoscope and in front of an image capturing unit or an eyepiece, wherein the filter arrangement can be configured to perform a change from a first filter property to a second filter property when the filter arrangement is rotated by 90° about the axis of rotation from a first target rotational position to a second target rotational position.

A filter property is understood herein to mean the spectral or polar filter characteristic of the optical filter, meaning, among other things, in which wavelength range the filter is permeable. This can go from the infrared range through the ultraviolet range and can also include polarization filtering, for example for linear or circular polarization. However, the first and second filter properties must differ from each other.

A rotatable filter arrangement can be switched back and forth between a first filter property and a second filter property without leaving the beam path by simply rotating the filter arrangement by 90°. This ensures that a filtering of the light according to the requirements of the respective examination is ensured in each setting of the rotatable filter arrangement. Since the filter arrangement itself remains in the beam path, it is possible to implement this without changing the size of the endoscope or alternatively while keeping the increase in size low.

In one embodiment, the optical filter which has different filter properties in different directions can be configured as a cuboid filter with two main axes lying perpendicular to each other and to the axis of rotation, which main axes each thrust perpendicularly through two side faces of the cuboid filter which lie opposite each other, wherein the optical filter can be held rotatably about an axis of rotation in the holder, wherein the optical filter reaches the two different target rotational positions by rotating the filter arrangement about the axis of rotation by 90°, in which in each of the positions one of the two main axes of the optical filter is arranged parallel to the optical axis of the at least one beam path.

In this embodiment, the optical filter can be cuboid. This means that the four side faces can be basically rectangular and at right angles to each other. The top and bottom side of the filter through which the axis of rotation runs can also be rectangular and flat. The formulation "cuboid filter" requires, however, that the optical filter is configured massively, wherein the filter property can be achieved by a suitable coating of at least one side face each per main axis, possibly also both side faces per main axis.

The cuboid filter can have a sufficient width and height in the projection transverse to the direction of the beam path in both target rotational positions in order to cover the at least one beam path. During the rotation, the maximum width can be the width of the diagonal through the rectangular projection in the plane spanned by the two main axes and is thus at most 41% wider than the widest of the two side face pairs. The additional space required to enable the rotation of the cuboid prism can therefore be relatively small.

In embodiments, the cuboid filter can have a coating for the first filter property and the second filter property respectively on at least two side faces that adjoin each other and are parallel to the axis of rotation, wherein all four of the side faces which are parallel to the axis of rotation can have coatings, in each case opposite each other in pairs, for the first filter property and the second filter property respectively.

An adjustment of the focus of the endoscope optical element can be omitted when changing the filter property by rotating the filter arrangement if, according to embodiments, the cuboid filter has different thicknesses in the direction of the two main axes, which thicknesses are adjusted to the focus of the optical system of the endoscope at the different wavelengths of the first filter property and the second filter property.

In embodiments, the filter arrangement can have two, three or four flat optical filters which are held by the holder and are arranged rotated by 90° in relation to each other, wherein in the first target rotational position at least one of the flat optical filters with the first filter property can lie in the beam path and in the second target rotational position at least one other of the flat optical filters with the second filter property can lie in the beam path. This embodiment differs from the embodiment with the cuboid filter in that the flat optical filters substitute for the side faces of the cuboid filter. The minimum number of optical filters in this case can be two optical filters which are arranged on the sides of a rectangle rotated by 90° in relation to each other so that when the filter arrangement is rotated, at least one of the two optical filters can be inserted into the beam path and the respective other can be positioned parallel to the beam path outside of the beam path. Due to the low optical thickness of the flat optical filter, it is also not necessary to refocus when changing the filter property i.e. rotating the filter arrangement.

The axis of rotation of the filter arrangement can be oriented perpendicular to the at least one beam path of the endoscope.

The aforementioned embodiments can be used both in endoscopes with one beam path and in stereo endoscopes which have, possibly in sections, two separate optical beam paths. The filter arrangement can thus also be arranged at a point in the endoscope at which a division into two parallel beam paths has not yet taken place. If necessary, one filter arrangement can also be used for each beam path.

In one embodiment, the endoscope can be configured as a stereo endoscope with two parallel beam paths and the filter arrangement can be configured as a filter wheel with two pairs of filters, wherein the filters of a first filter pair can have the first filter property and the filters of a second filter pair can have the second filter property, wherein the axis of rotation of the filter arrangement can correspond to a central axis between the beam paths and/or can lie parallel to the central axis, wherein the filters of the first filter pair can align with the beam paths in the first target rotational position and the filters of the second filter pair can align with the beam paths in the second target rotational position. In contrast to the prior art, the filter wheel here can be arranged with its two pairs of optical filters in the beam paths of the stereo endoscope where there is sufficient space for the filter wheel. A filtering of the illumination light is not necessary so the loss of illumination intensity can be limited.

In embodiments, an adjusting device can be provided on the endoscope by means of which the filter arrangement can be rotated. The adjusting device can be located on the handle or in a control device for the endoscopic system and enables switching between the target rotational positions and thus from the first filter property to the second filter property and back.

In embodiments, the adjusting device can comprise an adjusting ring configured as an outer magnetic ring which is operatively connected to an inner magnetic ring as part of a magnetic coupling, which inner magnetic ring is operatively connected to the holder of the filter arrangement, such as via a mechanical unit, such as a gear wheel mechanical unit. Rotary magnetic couplings are known in endoscopes. They have an outer adjusting ring that can be grasped with the hand and can be configured as a magnetic ring, and an inner magnetic ring in the hermetic part of the endoscope which produce a magnetic field geometry that can vary in the circumferential direction via the arrangement of magnet pole pieces or individual magnets distributed around the circumference. This inhomogeneity ensures that a rotation of the outer magnetic ring leads to an equally large rotation of the inner magnetic ring which can be transferred mechanically to the holder of the optical filter arrangement. In the case of a filter wheel, the inner magnetic ring can also be part of the filter wheel.

Alternatively, it is provided that the adjusting device can comprise an electric motor and a control unit for the motor control as well as an operating unit.

To ensure a secure placement of the respective holder of the optical filter arrangement in the two alternative target rotational positions, a latching mechanism can be configured to fix the filter arrangement in the first target rotational position or in the second target rotational position until a force is applied that overcomes the fixing.

Finally, such object can also be solved by a use of an optical filter arrangement in a previously described endoscope which comprises a holder that has an optical filter which has different filter properties in different directions, or holds multiple optical filters with different filter properties, wherein the filter arrangement is arranged rotatably about an axis of rotation in at least one beam path of the endoscope in the direction of light incidence in or behind an objective of the endoscope and in front of an image capturing unit or an eyepiece, wherein the filter arrangement can be configured to perform a change from a first filter property to a second filter property when the filter arrangement is rotated by 90° about the axis of rotation from a first target rotational position to a second target rotational position.

The use relates to the endoscope a and therefore shares its advantages, properties and features.

Further features of the embodiments will become apparent from the description of the embodiments together with the claims and the attached drawings. Embodiments can fulfill individual features or a combination of several features.

BRIEF DESCRIPTION OF THE DRAWINGS

The embodiments are described below, without restricting the general idea of the invention, based on exemplary embodiments in reference to the drawings, whereby we expressly refer to the drawings with regard to all details that are not explained in greater detail in the text. In the figures.

DETAILED DESCRIPTION

Figure 1:
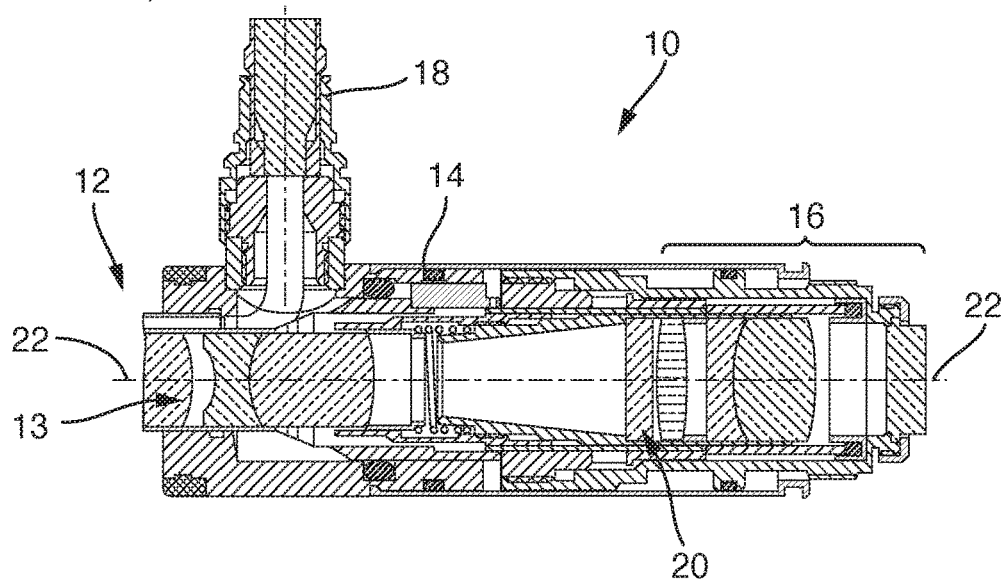
FIG. 1 illustrates a schematic cross-sectional diagram through a part of an endoscope according to the state of the art.

In the drawings, the same or similar elements and/or parts are provided with the same reference numbers in each case; a reintroduction will therefore always be omitted.

Figure 2A:
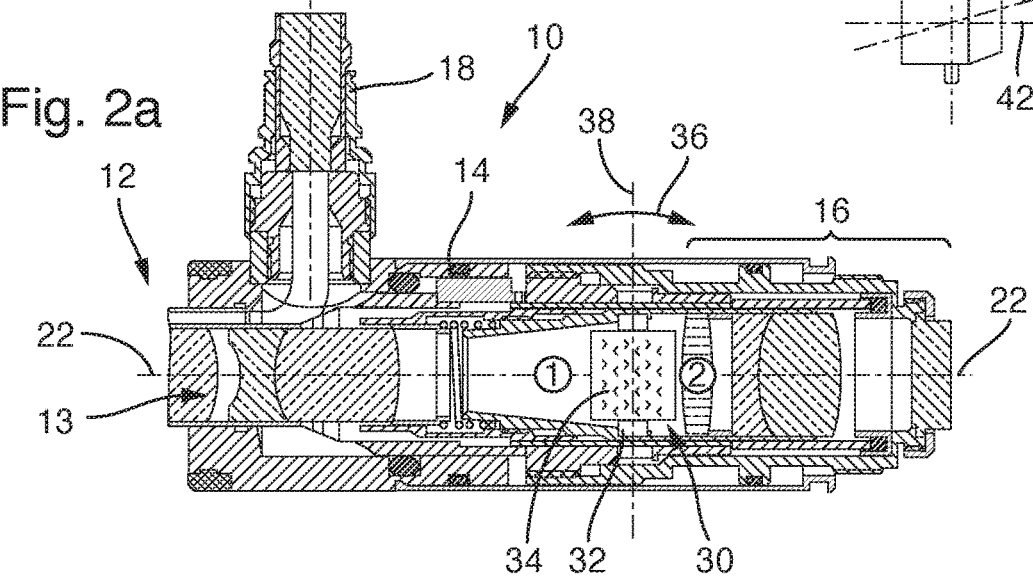
FIGS. 2a and 2b illustrate a schematic cross-sectional diagram through a part of an endoscope with a rotatable filter arrangement as well as a schematic diagram of the filter arrangement.

FIG. 2a shows a modified endoscope as compared to the known endoscope shown in FIG. 1, in which the IR filter 20 is replaced by an optical filter arrangement 30 which can be rotated about an axis of rotation 38. The optical filter arrangement 30 comprises a holder 32 which allows the rotation 36 about the axis of rotation 38 and holds a cuboid optical filter 34 which is shown principally schematically in FIG. 2b.

The cuboid optical filter 34 has two main axes 40, 42 that lie perpendicular to the axis of rotation 38 and to each other. These run centrally through the side faces of the cuboid optical filter 34. By rotating the optical filter 34 about the axis of rotation 38 by 90°, the main axis 40 or the main axis 42 are alternately brought parallel to the optical axis of the optical system of the endoscope 10 so that only the coatings on the inlet and/or outlet faces of the optical filter 34 that are active in each case ensure the filter effect with the filter property set in each case. Of the two side faces through which the main axis 40 runs, at least one is coated so that the first filter property is set, while of the two side faces through which the main axis 42 runs, at least one is coated so that the second filter property is set. The first filter property can be, for example, permitting the passage of visible light and blocking IR light, while the second filter property is permitting the passage of infrared light. The embodiments are not limited to a specific selection or combination of filter properties; the filter properties simply have to differ from each other..

Figure 3:
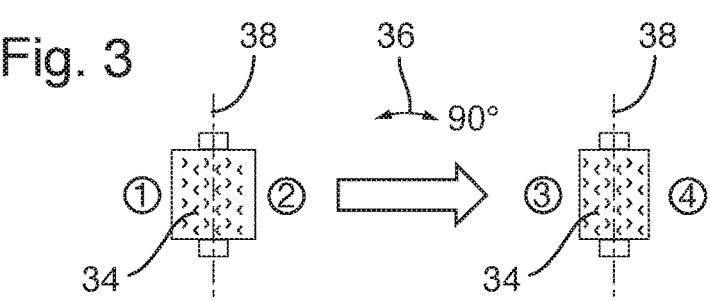
FIG. 3 illustrates a schematic diagram of the rotation of a rotatable filter arrangement.

FIG. 3 shows the effect of a 90° rotation 36 about the axis of rotation 38 of the optical filter 34. In a first state, the side faces 1 and 2 and, in a second state, the side faces 3 and 4 are thus located in the beam path, wherein, on the one hand, the side faces 1 and 2 lie opposite each other and, on the other hand, the side faces 3 and 4 lie opposite each other. In the first state or target rotational position, the optical filter 34 has a greater thickness than in the second state or the second target rotational position. The thicknesses in both directions are chosen so that a rotation can occur without refocusing the optical system, hence is adjusted to the filter property.

Figure 4:
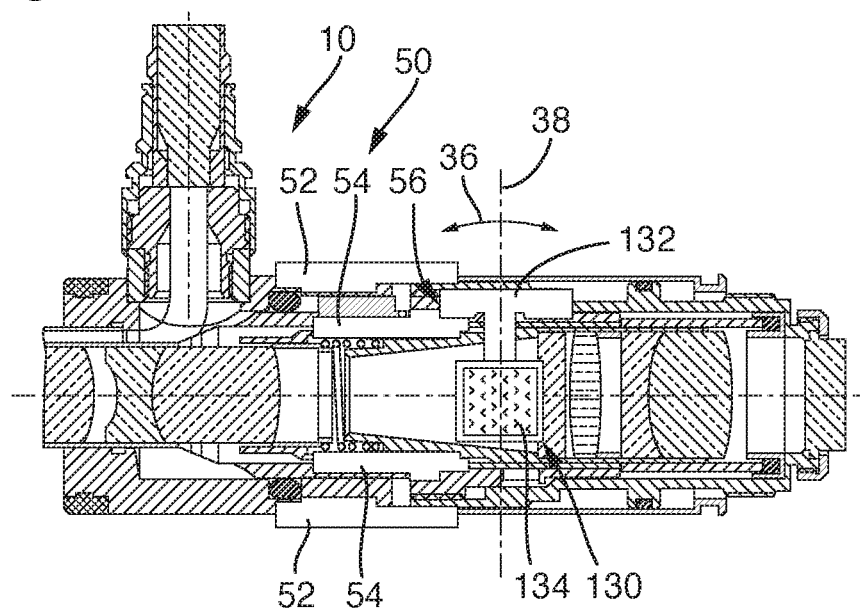
FIG. 4 illustrates a schematic cross-sectional diagram through a part of an endoscope with a further filter arrangement.

FIG. 4 shows another exemplary embodiment of an endoscope 10 with a rotatable filter arrangement 130. In contrast to the filter arrangement 30 according to FIGS. 2 and 3, multiple planar or flat optical filters 134, 136, possibly also 138, 140, are arranged in the holder 132, which generate the first or second filter property respectively. These planar filters 134, 136 are arranged rotated by 90° in relation to each other and correspond to the side faces of a cube.

Figure 2B:
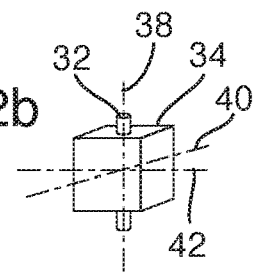

An adjusting device 50 with an adjusting mechanism is also shown in FIG. 4 which can also be used for the embodiment in FIGS. 2a, 2b and 3. This is a magnetic coupling which has an outer magnetic ring 52 as an adjusting ring that can be grasped by the hand of an operator and rotated about the longitudinal axis of the endoscope, as well as an inner magnetic ring 54 that interacts magnetically with the former and is entrained by the rotation of the outer magnetic ring 52. The inner magnetic ring has a gear wheel profile on its proximal end which forms a gear wheel mechanism or a gear wheel mechanical unit 56 in conjunction with a gear wheel profile on the holder 132. A rotation of the inner magnetic ring 54 about the optical axis or central axis of the endoscope therefore ensures that the holder 132 with the optical filters arranged on the holder is rotated about the axis of rotation 38 which is perpendicular to the optical axis.

Figure 5A:
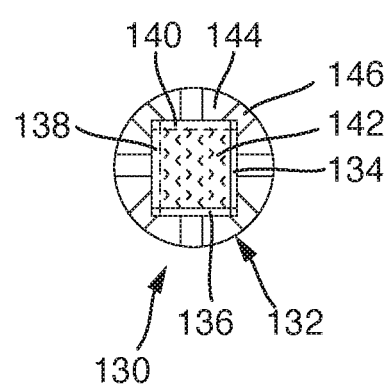
FIGS. 5a and 5b illustrate a schematic diagram of the filter arrangement according to FIG. 4.
Figure 5B:
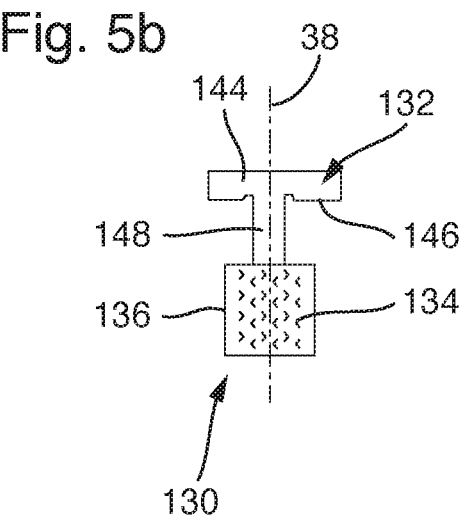

The holder 132 itself is shown in more detail in FIGS. 5a and 5b. The holder 132 comprises a holder disc 144 which has the gear wheel profile 146 as well as a central holder shaft 148 that comes out from the holder disc 144 and has the 2, 3 or 4 optical filters 134, 136, possibly 138, 140, on its other end. There is no material in the empty space between the optical filters 134, 136, 138, 140. The fact that the second optical filter 138, 140 s in each of the two pairs is optional is made clear in FIG. 5a in that these are only indicated with dashed lines.

Grooves can also be applied on the circumference of the holder disc 144 at a distance of 90° to each other, which grooves work together with a spring latching mechanism (not shown) to ensure a secure positioning of the filter arrangement in the target rotational positions.

Figure 6:
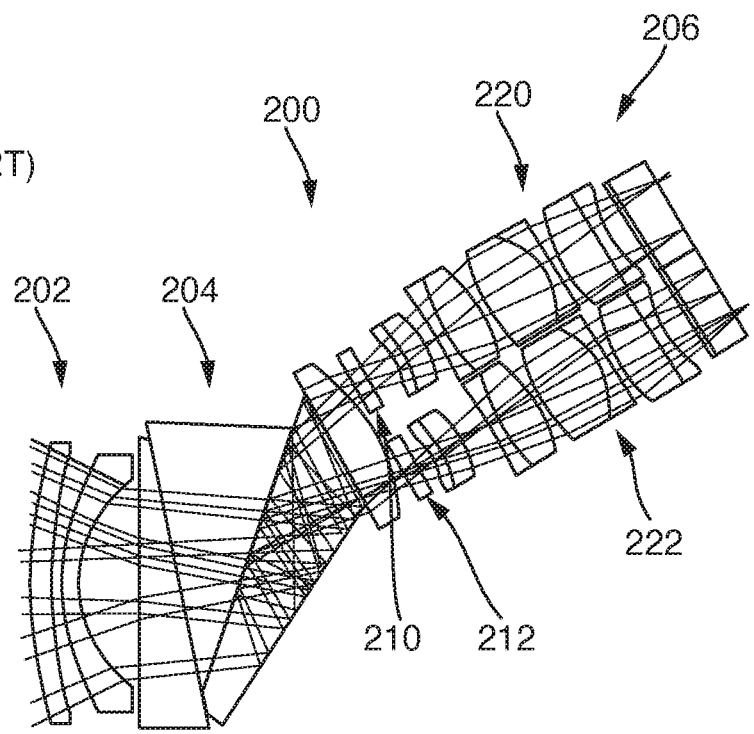
FIG. 6 illustrates a beam path of a sideways-facing stereo endoscope according to the state of the art.
Figure 7A:
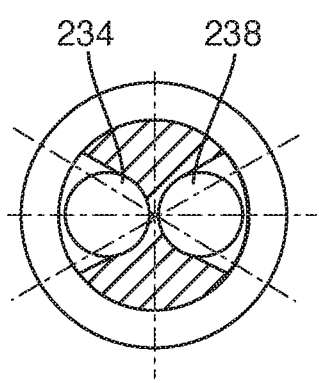
FIGS. 7a and 7b illustrate schematic diagrams of the filters of FIG. 6 and a filter wheel for replacement in a beam path according to FIG. 6, respectively.
Figure 7B:
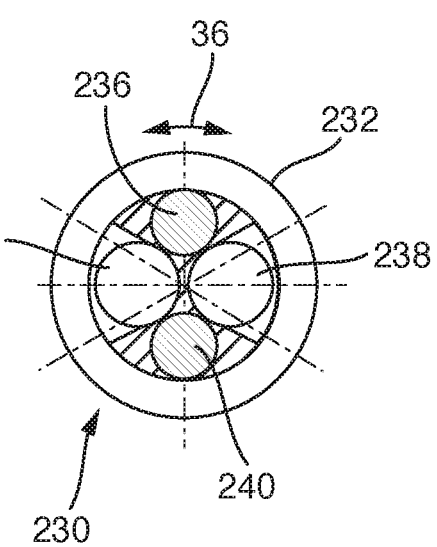

The filter arrangement 230 shown in FIG. 7b, can be used in FIG. 6 to replace the filter arrangement of FIG. 7a, where FIG. 7b illustrates a filter wheel 232 which can be rotated (reference sign 36) about the axis of rotation (without reference sign) running in the normal of the imaging plane, wherein a 90° rotation rotates the two filters 234, 238 out of the beam paths and the filters 236, 240 into the beam paths. A change in the geometry is not required for this. The filter wheel 232 can be mechanically connected to the inner magnetic ring 54 from the exemplary embodiment in FIG. 4 or comprise it. The filter wheel 232 can have grooves or similar means at a distance of 90° for a latching mechanism.

In the case that the optical system shown is arranged on the distal end of a long endoscope shaft, a mechanical connection through the endoscope shaft for the rotation of the filter wheel 232 can also be provided, or an electric adjusting motor can be provided or other suitable means can be used.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the

LIST OF REFERENCE SIGNS

10 Endoscope
12 Shaft
13 Objective
14 Housing
16 Eyepiece
18 Illumination unit
20 Optical filter
22 Optical axis
30 Optical filter arrangement
32 Holder
34 Optical filter
36 Rotation
38 Axis of rotation
40, 42 Main axis
50 Adjusting device
52 Adjusting ring
54 Inner magnetic ring
56 Gear wheel mechanical unit
130 Optical filter arrangement
132 Holder
134, 138 Optical filter
136, 140 Optical filter
142 Empty space
144 Holder disc
146 Gear wheel profile
148 Holder shaft
200 Optical system of a stereo endoscope
202 Input lens system
204 Deflection prisms
206 Parallel lens systems
210, 212 Optical filter
220 First beam path
222 Second beam path
230 Optical filter arrangement
232 Filter wheel
234, 238 Optical filter
236, 240 Optical filter

What is claimed is:

1. An endoscope comprising:
one or more optical lenses disposed along an optical axis,
  a beam path through the one or more lenses extending from an objective to an image capturing unit or an eyepiece; and
an optical filter arrangement comprising:
  a holder disposed in an interior of the endoscope in the at least one beam path and outside of the image capturing unit or the eyepiece, the holder being rotatable about an axis of rotation perpendicular to the optical axis; and
  an optical filter arranged in the holder, the optical filter having one of different filter properties in different directions or multiple optical filters with different filter properties, the optical filter having a plurality of external faces rotated by 90° in relation to each other about the axis of rotation of the holder, each of the different filter properties corresponding to a different external face of the optical filter,
an adjusting device configured to rotate the optical filter arrangement, wherein the adjusting device comprises a magnetic coupling having an outer magnetic ring and an inner magnetic ring operatively coupled to an outer magnetic ring, the inner magnetic ring being operatively coupled to the holder such that rotation of the outer magnetic ring rotates the optical filter arrangement;
wherein the optical filter arrangement is configured to change from a first filter property to a second filter property when the optical filter is rotated by 90° about the axis of rotation from a first target rotational position to a second target rotational position; and
light is incident on a first external face of the plurality of external faces in the first target rotational position and the light is incident on a second external face of the external plurality of faces, different from the first external face, in the second target rotational position.

2. The endoscope according to claim 1, wherein the optical filter, which has different filter properties in different directions, is configured as a cuboid filter with two main axes lying perpendicular to each other and to the axis of rotation, the two main axes each thrust perpendicularly through two side faces of the cuboid filter which lie opposite each other, wherein the optical filter is held rotatably about the axis of rotation in the holder, and the optical filter reaches the two different target rotational positions by rotating the filter arrangement about the axis of rotation by 90°, in which each of the positions of the two main axes of the optical filter is arranged parallel to the optical axis of the at least one beam path.

3. The endoscope according to claim 2, wherein the cuboid filter has a first coating for the first filter property and a second coating on the second filter property respectively on at least two side faces that adjoin each other and are parallel to the axis of rotation.

4. The endoscope according to claim 3, wherein third and fourth side faces of the cuboid filter which are parallel to the axis of rotation have third and fourth coatings, respectively, wherein the first filter property comprises two of the first, second, third and fourth filters opposite each other on the cuboid filter and the second filter property comprises another two of the first, second, third and fourth filters opposite each other on the cuboid filter.

5. The endoscope according to claim 2, wherein the cuboid filter has different thicknesses in the direction of the two main axes, the different thicknesses are selected to correspond to a focus of the optical system of the endoscope at different wavelengths of the first filter property and the second filter property.

6. The endoscope according to claim 1, wherein the filter arrangement has two, three or four flat optical filters held by the holder, the two, three or four flat optical filters being rotated by 90° in relation to each other, wherein in the first target rotational position at least one of the two, three or four flat optical filters with the first filter property lies in the beam path and in the second target rotational position at least one other of the two, three or four flat optical filters with the second filter property lies in the beam path.

7. The endoscope according to claim 1, wherein the axis of rotation of the filter arrangement is oriented perpendicular to the at least one beam path of the endoscope.

8. The endoscope according to claim 1, wherein the endoscope is configured as a stereo endoscope with two parallel beam paths and the filter arrangement is configured as a filter wheel with two pairs of filters, wherein one of the two pairs of filters have the first filter property and an other of the two pairs of filters pair have the second filter property, the axis of rotation of the filter arrangement corresponds to one or more of a central axis between the beam paths and lies parallel to the central axis, and the one of the two pairs of the filters align with the beam paths in the first target rotational position and the other of the two pairs of the filters align with the beam paths in the second target rotational position.

9. The endoscope according to claim 1, wherein the inner magnetic ring is coupled to the holder via a gear wheel mechanical unit.

10. The endoscope according to claim 1, wherein the adjusting device comprises an electric motor and a control unit for the motor control as well as an operating unit.

11. The endoscope according to claim 1, further comprising a latching mechanism configured to fix the filter arrangement in the first target rotational position or in the second target rotational position.

12. A method of using an endoscope, wherein the endoscope comprising:
   one or more optical lenses disposed along an optical axis, a beam path through the one or more lenses extending from an objective to an image capturing unit or an eyepiece; and
   an optical filter arrangement comprising:
      a holder disposed in an interior of the endoscope in the at least one beam path and outside of the image capturing unit or the eyepiece, the holder being rotatable about an axis of rotation perpendicular to the optical axis; and
      an optical filter arranged in the holder, the optical filter having one of different filter properties in different directions or multiple optical filters with different filter properties, the optical filter having a plurality of external faces rotated by 90° in relation to each other about the axis of rotation of the holder, each of the different filter properties corresponding to a different external face of the optical filter,
   an adjusting device configured to rotate the optical filter arrangement, wherein the adjusting device comprises a magnetic coupling having an outer magnetic ring and an inner magnetic ring operatively coupled to an outer magnetic ring, the inner magnetic ring being operatively coupled to the holder such that rotation of the outer magnetic ring rotates the optical filter arrangement;
   wherein the optical filter arrangement is configured to change from a first filter property to a second filter property when the optical filter is rotated by 90° about the axis of rotation from a first target rotational position to a second target rotational position;
   the method comprising:
      changing from the first filter property to the second filter property when the optical filter is rotated by 90° about the axis of rotation from the first target rotational position to the second target rotational position, and
      light is incident on a first external face of the plurality of external faces in the first target rotational position and the light is incident on a second external face of the plurality of external faces, different from the first external face, in the second target rotational position;
      wherein the changing comprises rotating the optical filter arrangement by 90° about the axis of rotation by rotating the outer magnetic ring.

* * * * *